US006795172B2

(12) United States Patent
Putman et al.

(10) Patent No.: US 6,795,172 B2
(45) Date of Patent: Sep. 21, 2004

(54) METHOD FOR PREPARING A CUT SURFACE IN UNCURED RUBBER SAMPLES FOR MEASURING FILTER DISPERSION

(75) Inventors: John B. Putman, Cuyahoga Falls, OH (US); Matthew C. Putman, Stow, OH (US); Joseph G. Bulman, Kent, OH (US)

(73) Assignee: Tech Pro, Inc., Cuyahoga falls, OH (US)

( * ) Notice: Subject to any disclaimer, the term of this patent is extended or adjusted under 35 U.S.C. 154(b) by 305 days.

(21) Appl. No.: 09/978,501

(22) Filed: Oct. 16, 2001

(65) Prior Publication Data

US 2003/0090648 A1 May 15, 2003

(51) Int. Cl.[7] .......................... G01N 1/00; G01N 21/55
(52) U.S. Cl. ........................................ 356/36; 356/445
(58) Field of Search ............................... 356/36, 237.1, 356/237.3, 238.2, 238.3, 445–448, 342, 347; 382/141; 204/475, 476; 425/200, 202; 83/15, 17–20

(56) References Cited

U.S. PATENT DOCUMENTS

| | | | | |
|---|---|---|---|---|
| 3,640,127 A | * | 2/1972 | Meissner | 73/789 |
| 3,897,190 A | * | 7/1975 | Binzburg et al. | 425/383 |
| 3,975,127 A | * | 8/1976 | Munk et al. | 425/193 |
| 4,220,042 A | * | 9/1980 | Vegvari et al. | 73/150 R |
| 4,245,517 A | * | 1/1981 | Barker et al. | 73/760 |
| 5,974,167 A | * | 10/1999 | Reszler | 382/141 |
| 6,526,859 B1 | * | 3/2003 | Ozawa et al. | 87/35 |

OTHER PUBLICATIONS

A.Y. Coran and J.B Connet, Rubber Chem. and Technology, vol. 65, pp. 973–997, (1992).
P.S. Johnson, "Basic Compounding and Processing of Rubber", Harry Long, Ed., Rubber Division, American Chemical Society, 1997, p. 52.
F.S. Myers and S. W. Newell, Paper No. 38, 111th Spring Technical Meeting, Rubber Division, American Chemical Society, Chicago, IL, May 1977.

(List continued on next page.)

Primary Examiner—Zandra V. Smith
Assistant Examiner—Gordon J. Stock, Jr.
(74) Attorney, Agent, or Firm—Renner, Kenner, Greive, Bobak, Taylor & Weber

(57) ABSTRACT

A method for cutting compounded rubber for reflected light measurement of the disbursement of fillers therein is disclosed. The method includes subjecting a sample of compounded rubber to a dynamic pulling force, and cutting the sample while it is subjected to the dynamic pulling force. The method may further include the step of pressing the sample to remove entrapped air from the sample, and, preferably, the method includes cooling the sample during such a pressing step. Cutting the sample while it is subjected to a dynamic pulling force will reduce, and, preferably, eliminate, the presence of smears on a cut surface of the sample. By reducing the amount of entrapped air within a sample and, further, reducing the occurrence of smearing during cutting of the sample, a subsequent reflected light measurement of the dispersion of fillers within the compounded rubber sample is more accurate.

8 Claims, 12 Drawing Sheets

OTHER PUBLICATIONS

G.E. O'Conner and J.B. Putman, Rubber Chem. Technology, vol. 51, p. 799, (1978).

P.S. Johnson, "Basic Elastomer Technology", K.C. Baranwal, H.L. Stephens, Eds., The Rubber Division, American Chemical Society, 2001, pp. 118–120.

ASTM D1566–00b, "Standard Terminology Relating", American Society for Testing and Materials, West Conshohocken, PA, 2001 p. 302.

R.W. Jones, *Rubber Age*, Sep. 1968, pp. 52–57.

A.B. Sullivan and R.W. Wise, "Rubber Technology", M. Morton, Ed., $3^{rd}$ Ed., Van Nostrand Reinhold, NY, 1987, pp. 105–108.

W. Cousins and J. Dick, *Rubber World*, Jan. 1998, pp. 28–35.

H. Burhin, W. Spreutels and J. Sezna, Paper No. 74, The Spring Technical Meeting, Rubber Division, American Chemical Society, Detroit, MI, Oct. 1989.

B.B. Boonstra, "Rubber Technology", M. Mortion, Ed., $2^{nd}$ ed., Van Nostrand Reinhold, NY, 1973, p. 70.

W.M. Hess, Rubber Chem. Technology, vol. 64, p. 387, (1991).

P. Lovgren and S. Persson, *Tire Technology International*, 1994.

ASTM D2663–95a, Standard Test Methods for Carbon Black–Dispersion, vol. 09.01, American Society for Testing and Materials, West Conshohocken, PA, pp. 401–411 (2001).

ASTM D1646—00, "Standard Test Methods for Rubber–Viscosity, Stress Relaxation, and Pre–Vulcanization Characteristics (Mooney Viscometer)", vol. 09.01, American Society for Testing and Materials, West Conshohocken, PA, pp. 318–329, (2001).

P.R. van Buskirk, S.B. Turtzdky and P.F. Gunberg, Rubber Chem. and Technology, vol. 48, p. 590, (1975).

A.R. Payne, Rubber Chem. and Technology, vol. 39, pp. 365–374, (1996).

B.R. Richmond, Paper No. 68, The Spring Technical Meeting, Rubber Division, American Chemical Society, Denver, CO, May 1993.

J. Brennan and D.H. Lambert, Rubber Chem. and Technology, vol. 45, p. 105, (1972).

* cited by examiner

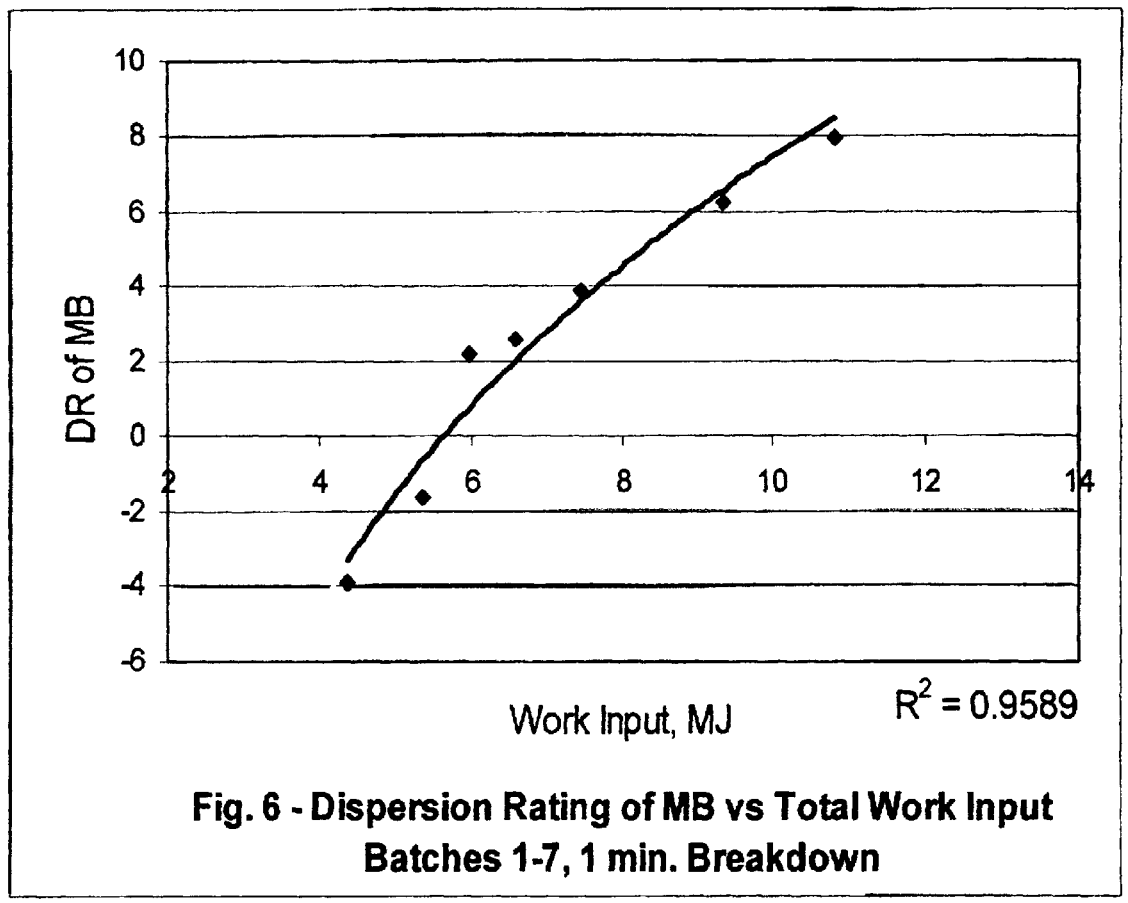
Fig. 6 - Dispersion Rating of MB vs Total Work Input
Batches 1-7, 1 min. Breakdown

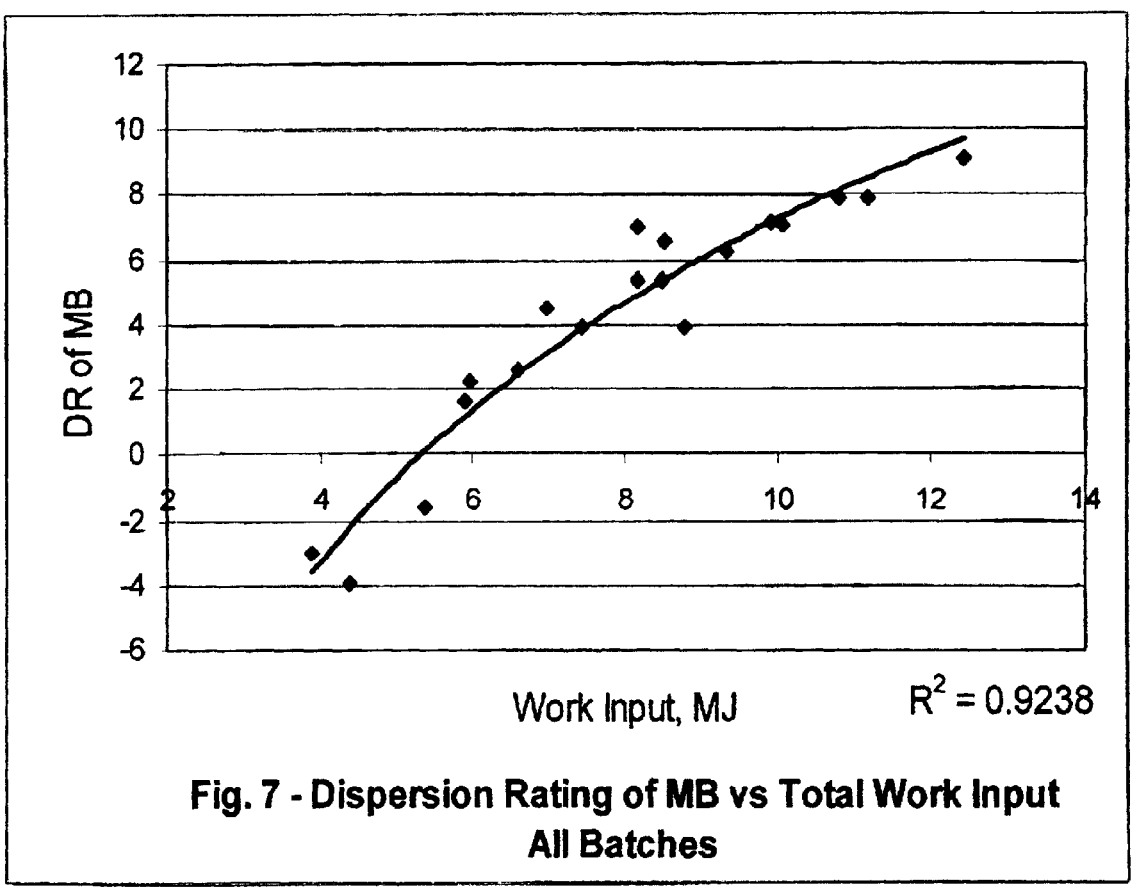
Fig. 7 - Dispersion Rating of MB vs Total Work Input
All Batches

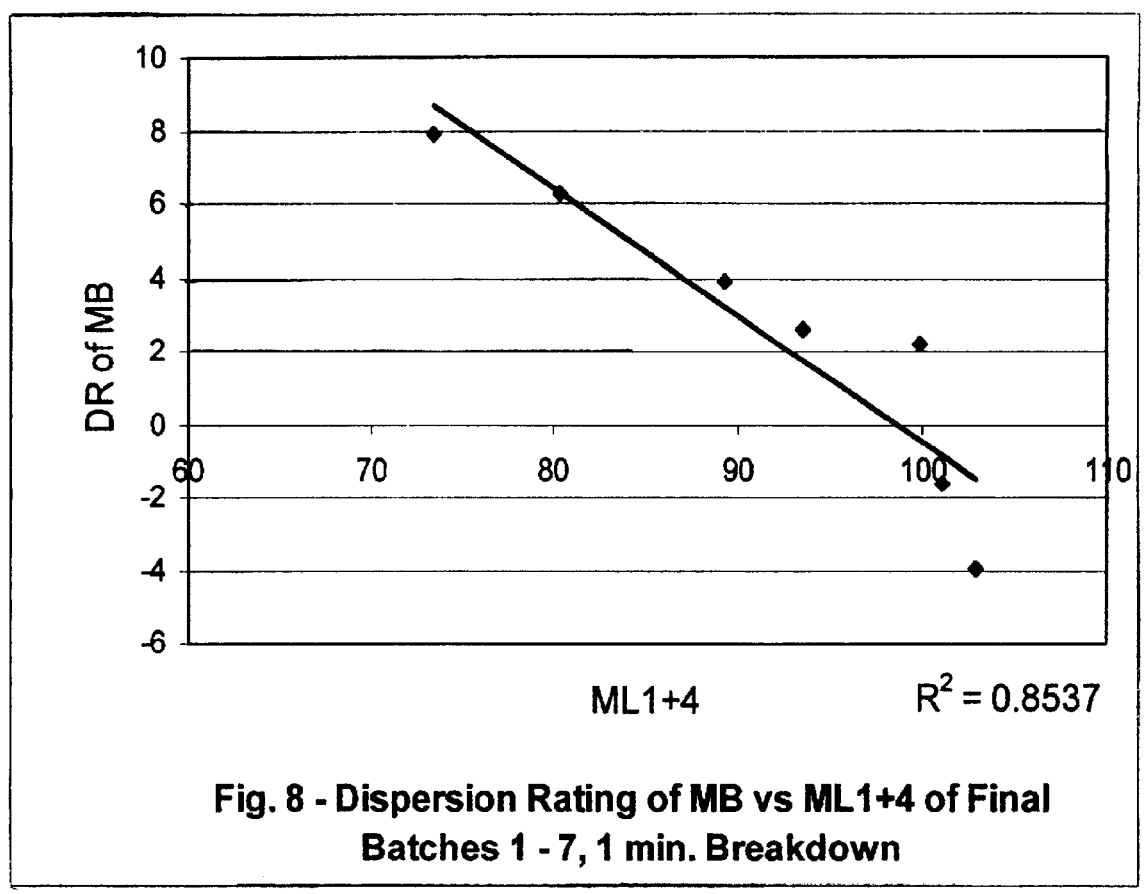
Fig. 8 - Dispersion Rating of MB vs ML1+4 of Final Batches 1 - 7, 1 min. Breakdown

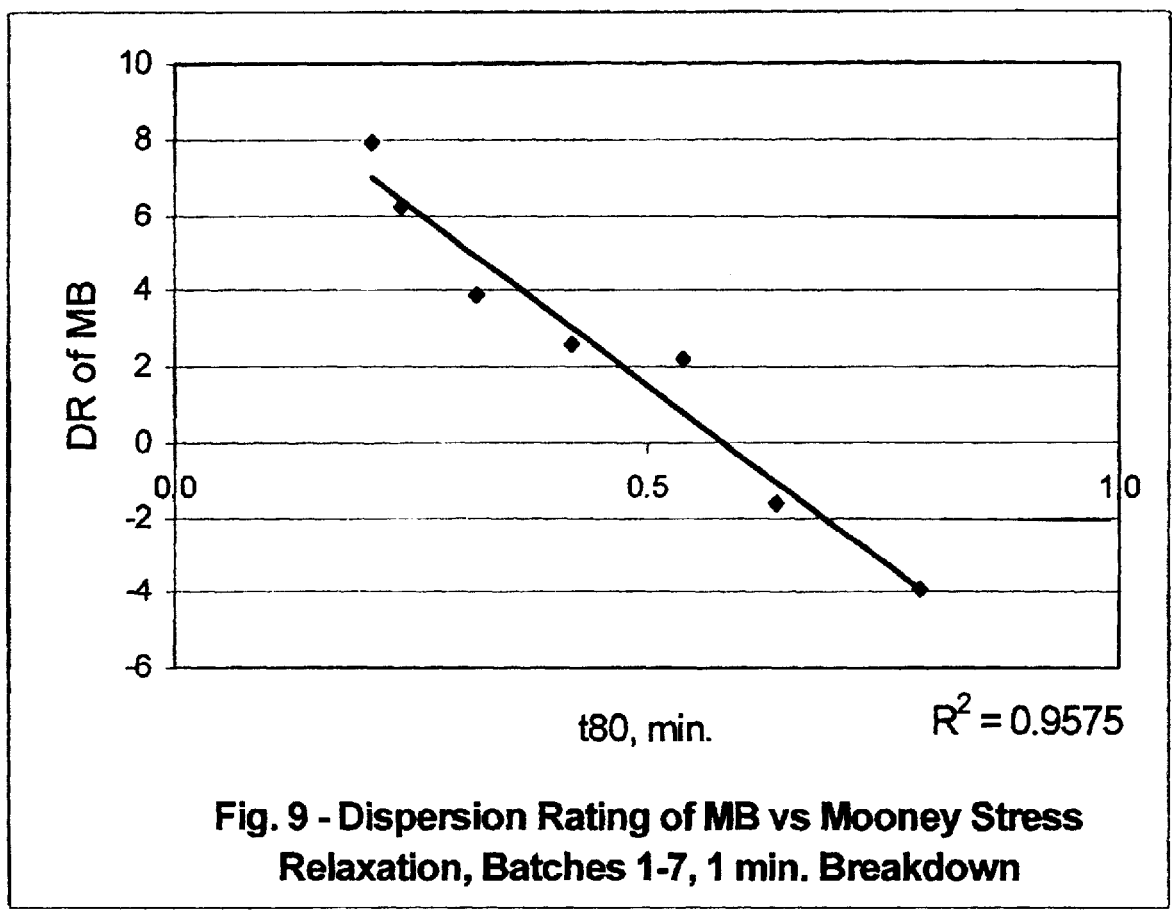
Fig. 9 - Dispersion Rating of MB vs Mooney Stress Relaxation, Batches 1-7, 1 min. Breakdown

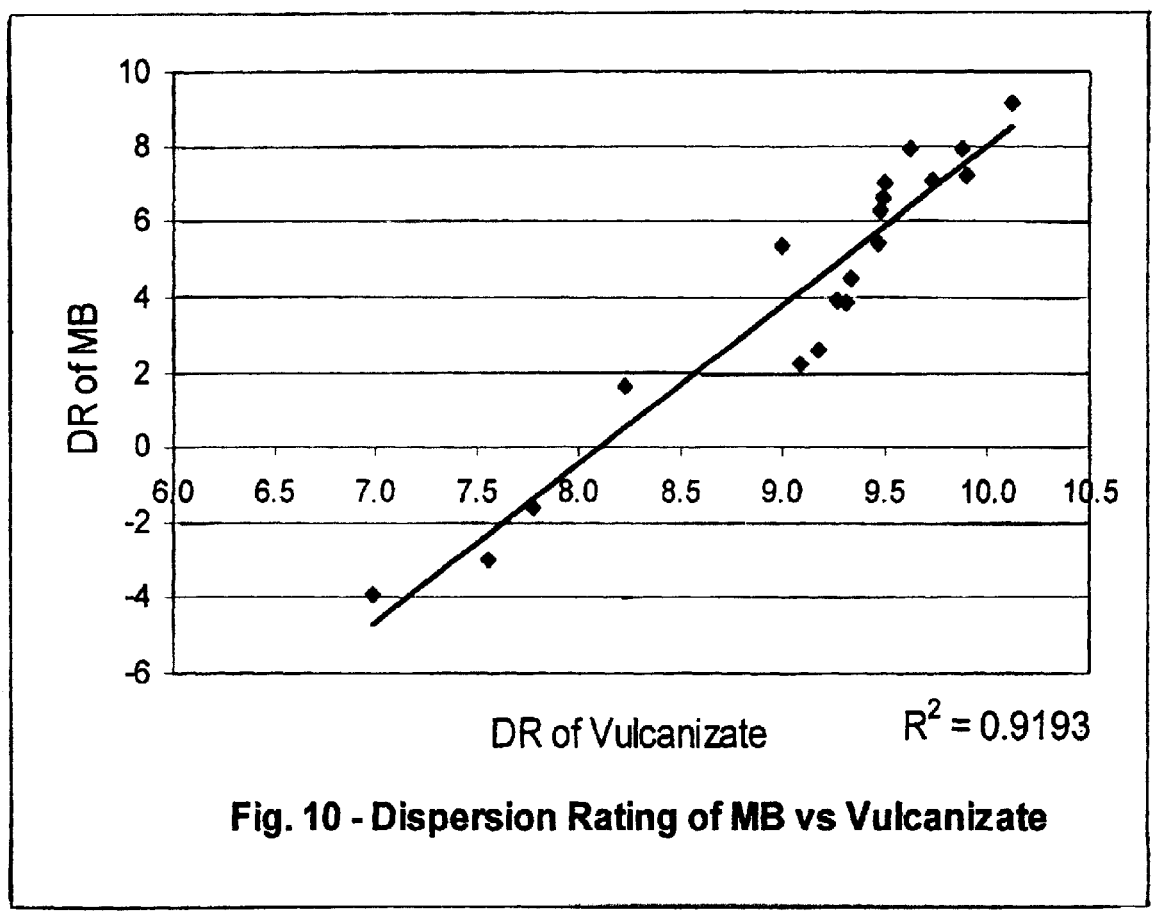
Fig. 10 - Dispersion Rating of MB vs Vulcanizate

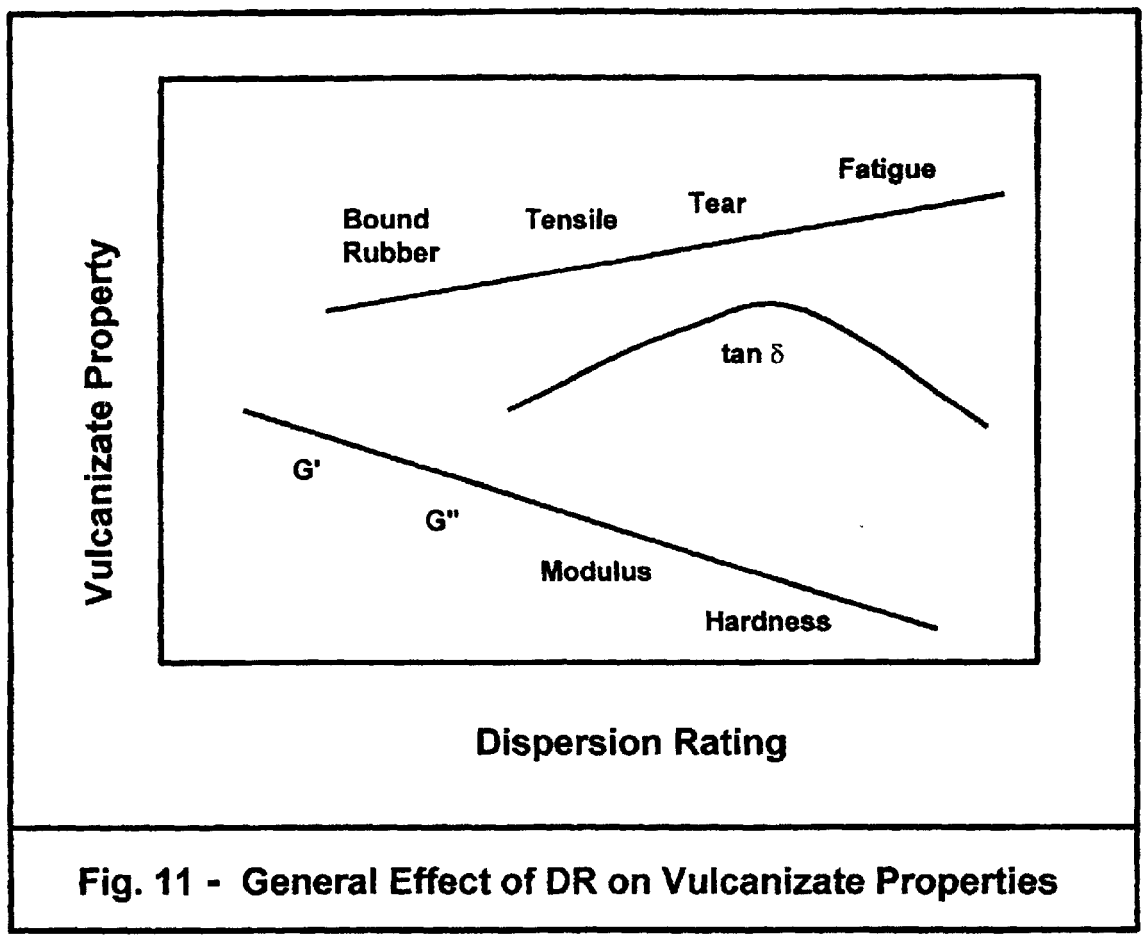
Fig. 11 - General Effect of DR on Vulcanizate Properties

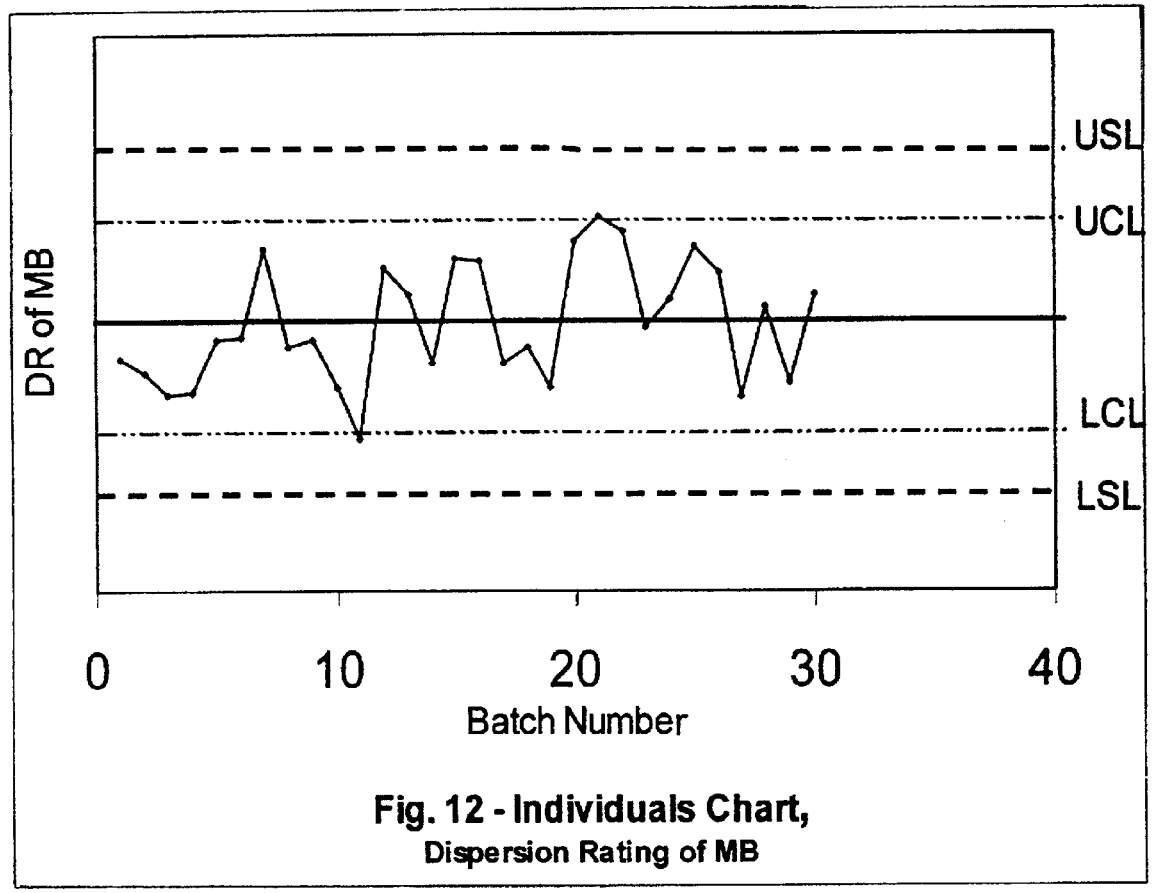
Fig. 12 - Individuals Chart,
Dispersion Rating of MB

METHOD FOR PREPARING A CUT SURFACE IN UNCURED RUBBER SAMPLES FOR MEASURING FILTER DISPERSION

BACKGROUND OF THE INVENTION

The present invention generally relates to a method for measuring filler dispersion in uncured rubber.

To prepare rubber compositions for end use applications, rubber compounds are commonly mixed with reinforcing fillers, such as carbon black; processing oils and waxes, processing aids, such as zinc oxide and stearic acid; and other known additives, such as pigments, plasticizers, antioxidants, vulcanizing agents and accelerators, and the like. Typically, the rubber, fillers, and other selected ingredients are first mixed together in a "masterbatch" to produce a uniformly blended compound in preparation for a second or final pass. In the final pass, the accelerators and curing agents are added so that the rubber compound may be vulcanized.

Quality control for rubber compounds focuses on the final mix, in order to assure that all ingredients have been incorporated into the compound in the proper proportions so as to produce a final product that will meet the quality requirements of the end user. Perhaps the most common quality control test of a final mix is the curemeter. The curemeter is typically run on compounds that have had accelerators and curing agents added, and are, thus, ready to go to final processing (i.e., shaping and vulcanization). The curemeter serves to identify those rubber compositions that are out of specification before they go into final processing, and also to make adjustments to the compounding process to assure correct future batches. In short, these tests are designed to "fingerprint" the batch (i.e., determine if it exhibits the desired properties at this testing stage). If the specific batch being tested matches the fingerprint, it is assumed that it will make an acceptable final product.

Processability tests are also employed in the quality control of rubber compounds. These tests are designed to determine the ability of the material to go through the intended forming processes, and are not specifically geared to assure that the final, cured rubber products will meet end-use specifications. These tests indicate the ability of compounded rubbers to be extruded, injection molded, or otherwise formed into final shapes. The Mooney viscosity test, the Mooney stress relaxation test, and DMRT instrument test are examples of such processability tests.

Curemeter and processability tests, while being useful for assuring quality end products, do not specifically address the mixing process and, more specifically, do not address the dispersion of the reinforcing fillers within compounded rubbers. Good filler dispersion is necessary because poor filler dispersion can lead to poor product appearance, poor processing and manufacturing uniformity, reduced product life and performance, and may also lead to a waste of raw materials and excessive energy usage during processing. Various methods have been developed to quantify the level of filler dispersion within compounded rubber. Of particular relevance to the method of the present invention is the reflected light measurement (RLM) method for measuring filler dispersion.

The RLM method for quantifying the level of filler dispersion within a compounded rubber composition will be generally appreciated with reference to FIGS. 1 and 2. FIG. 1 shows the cutting operation of a cutting blade 100 on a compounded rubber sample 102 containing reinforcing fillers 104. As the cutting blade 100 is advanced through the sample 102, it comes into contact with the fillers 104, and the fillers 104 are forced to move out of the path the cutting blade 100. This movement is represented by arrows A. Movement of the fillers 104 leaves behind either depressions 106 or a bumps 108 on the cut surfaces 110, 112 of the sample 102. The surface roughness resulting from the depressions 106 and bumps 108 thus relate to the level of filler dispersion, and the RLM method can be employed to measure the level of filler dispersion within the compounded rubber composition that provided the rubber sample 102.

Referring now to FIG. 2, the way in which the RLM method operates to quantify the level of filler dispersion within compounded rubber is generally depicted. Therein, a light source 116 sends beams of light 118, 120 toward the cut surface 110 of a rubber sample 102 that has been cut generally as described with reference to FIG. 1. The light beams 118 hit the cut surface 110 on an angle such that, when the light beams 118 reflect from either an indentation 106 or bump 108, the light 118 is reflected into a sensor 122 and, when light beams 120 are reflected from a smooth surface on cut surface 110, the reflected light is not picked up by sensor 122.

Light reflected back to sensor 122 thus indicates the existence of surface roughness, more particularly, the existence of a dispersed filler 104 within the rubber compound that provided the rubber sample 102. The amount and positioning of reflected light beams 118 picked up by sensor 122 is then compared to a standard set of images indicating dispersion ratings on a scale of 1 to 10, where 10 indicates very good dispersion.

However, in order to ensure that the results obtained from the reflected light measurement method are accurate and reliable, the cut surface 110 of the sample 102 must have a minimal amount of cut marks or smear marks, and the depressions therein should exist as a result of displaced filler, not entrapped air.

The present invention thus provides a method for measuring filler dispersion within uncured rubber through the reflected light measurement method, wherein cut rubber samples are prepared having minimal cut or smear marks and minimal depressions resulting from entrapped air within the rubber sample.

At least one method exists in the prior art for addressing these smear marks and entrapped air concerns. In this method, samples of compounded rubber are first pressed to remove entrapped air therefrom and, thereafter, the samples are pulled to about a 10% strain. Upon reaching this stretching point, the pulling action becomes static, and the sample is cut through the pressed portion. The stretching of the sample is performed in an attempt to prevent the creation of smear marks during cutting; however, it has been found that smear marks still result on the cut surfaces of the sample, due to the fact that, once the stretching action is allowed to go static, the rubber sample begins to relax and the cut surfaces do not sufficiently pull away from the cutting blade moving through the sample.

Thus, a need exists in the art for an improved method for cutting compounded rubber for reflected light measurement of the dispersion of fillers therein.

The need also exists for a device capable of carrying out the method disclosed herein.

SUMMARY OF THE INVENTION

In general, the present invention provides a method for cutting compounded rubber for reflected light measurement of the dispersion of fillers therein. The method includes subjecting a sample of compounded rubber to a dynamic pulling force; and cutting the sample for the purpose of analyzing the dispersion of fillers therein through reflected light measurement methods. Prior to subjecting the sample to a dynamic pulling force, the method may further include pressing the sample at the portion thereof that is to be cut in order to free the sample from entrapped air.

Pressing the sample at a portion thereof that is to be cut serves to minimize or eliminate the presence of entrapped air within the sample. Upon cutting the pressed sample, the cut surface will exhibit a minimal number of depressions, if any, resulting from cutting through air pockets therein. This will lead to a more accurate reflective light measurement of the dispersion of fillers within the sample because the depressions therein that reflect light back to the sensor will be the result of filler dispersion, not entrapped air.

Subjecting the sample to a dynamic pulling force during cutting also helps to ensure a more accurate reflected light measurement of filler dispersion, because cutting the sample in this manner either minimizes or eliminates the presence of smears on the cut surface. Particularly, as the cutting blade moves through a sample subjected to a dynamic pulling force, the cut portions of the sample tend to move away from the cutting blade due to the pulling force and the natural elasticity of the sample. The absence of smears on the cut surface of a sample also increases the accuracy of the reflected light measurement of filler dispersion, because smears present depressions and asperities on the cut surface that do not result from the presence of dispersed filler. The absence of smears helps to ensure that all light reflected back to the sensor reflects off of bumps or depressions created by dispersed fillers.

Notably, this method is preferably practiced on a masterbatch sample of rubber that is compounded with fillers. This method can serve as a direct indicator of the dispersion rating of the masterbatch and as an indirect indicator of the dispersion rating and physical properties of vulcanizates prepared from the masterbatch. The dispersion rating within the masterbatch can therefore be used as a process control measurement to indicate any needed changes in the mixing process. If the dispersion rating of the masterbatch does not correlate with desired end properties of a vulcanizate, the processing of the masterbatch can be adjusted to achieve the desired dispersion. Notwithstanding the foregoing, the method taught herein can also be employed with vulcanizate samples.

The present invention also provides a device for preparing a cut sample of compounded rubber in accordance with the method taught herein. Generally, the present invention provides a device for cutting compounded rubber for reflected light measurement of the dispersion of fillers therein. The device includes first and second clamps spaced apart across a gap for clamping a sample of compounded rubber across the gap. At least one of the first and second clamps is capable of moving relative to the other of the first and second clamps so as to alter the distance between the clamps for stretching a sample of compounded rubber clamped across the gap. A cutting blade is disposed in the gap for advancing through a sample of compounded rubber during the relative movement of the first and second clamps such that a sample of compounded rubber may be cut while being subjected to a dynamic pulling force.

BRIEF DESCRIPTION OF THE DRAWINGS

For a complete understanding of the objects, techniques and structure of the invention, reference should be made to the following detailed description and accompanying drawings wherein:

FIG. 6 is a graph of dispersion rating versus total work input for batches 1 through 7 in the Experimental section herein;

FIG. 7 is a graph of dispersion rating versus total work input for all batches in the Experimental section herein;

FIG. 8 is a graph of dispersion rating versus ML1+4 of final batches 1 through 7 in the Experimental section herein;

FIG. 9 is a graph of dispersion rating versus Mooney Stress Relaxation of batches 1 through 7 in the Experimental section herein;

FIG. 10 is a graph of dispersion rating of the masterbatch versus dispersion rating of the vulcanizate as in the Experimental section herein;

FIG. 11 is a graph of the general effect of dispersion rating on vulcanizate properties; and FIG. 12 is an Individual Chart, dispersion rating of the masterbatch, as in the Experimental section herein.

PREFERRED EMBODIMENT OF THE INVENTION

Figure 1:
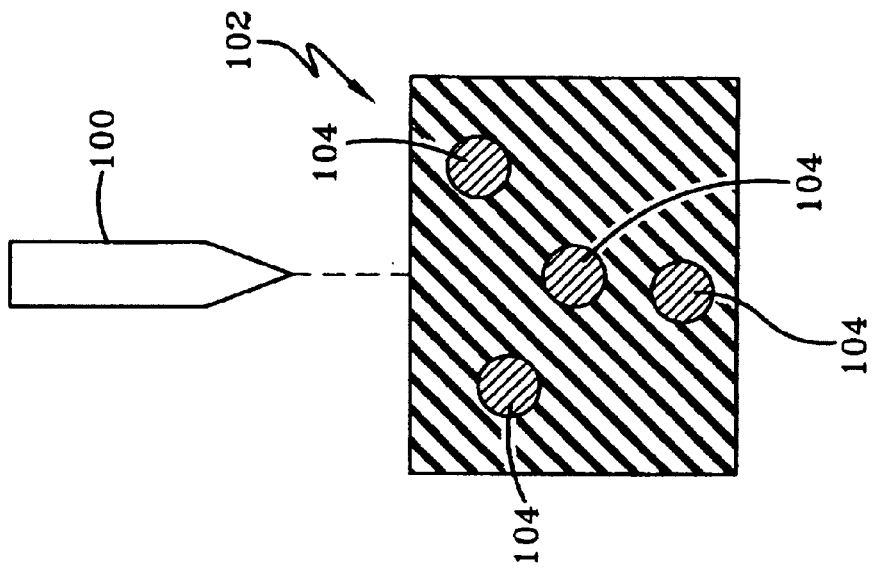
FIG. 1 generally represents the preparation of a cut surface in a compounded rubber sample for the purpose of measuring the dispersion of fillers therein through the reflected light measurement method.
Figure 1:
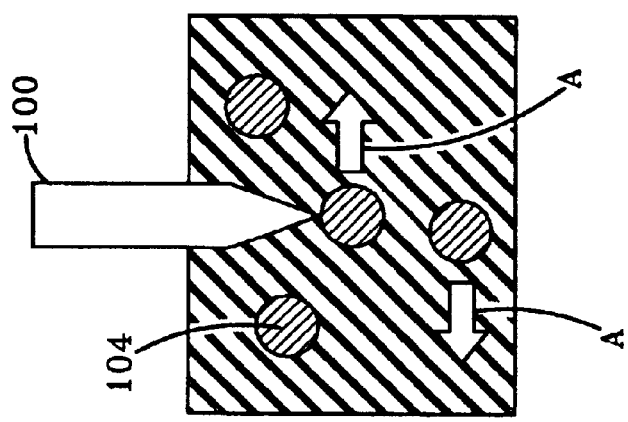
Figure 1:
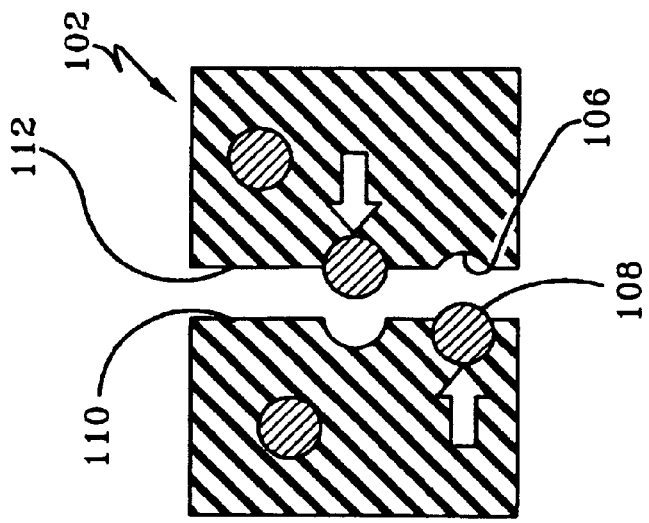
Figure 2:
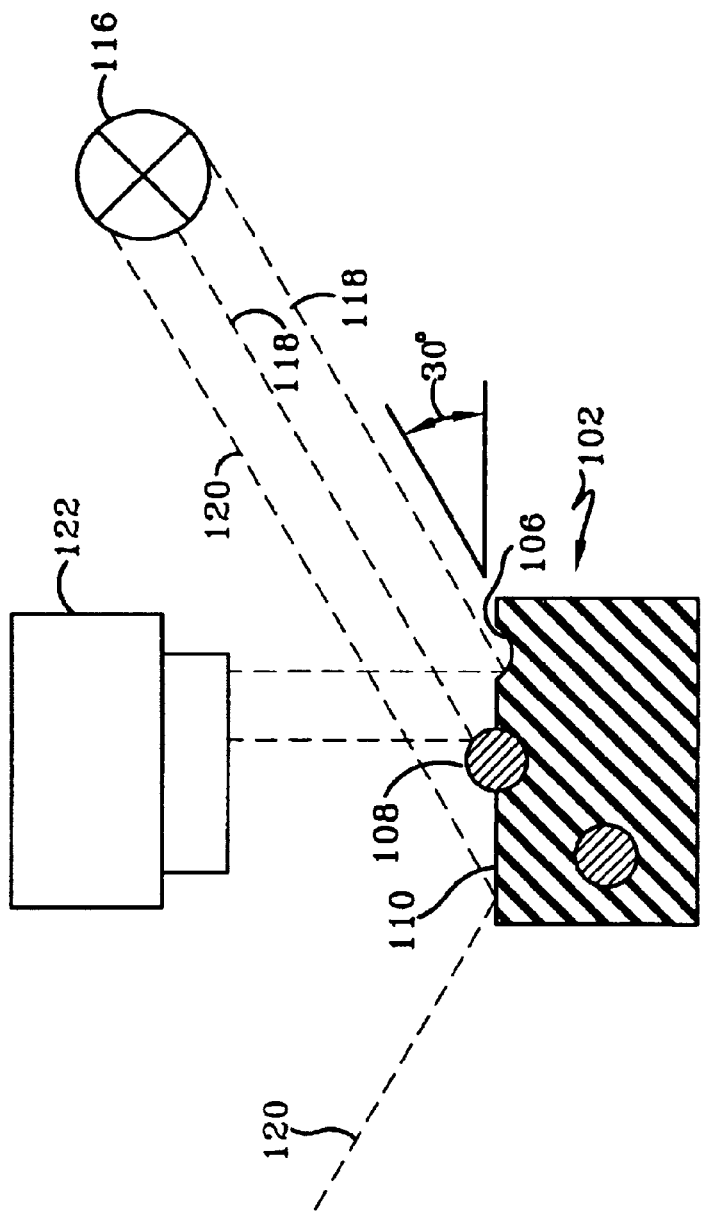
FIG. 2 generally represents the reflected light measurement method for measuring the dispersion of fillers in a compounded rubber sample.

The present disclosure serves to provide an improved method for preparing cut sample of compounded rubber for the measurement of the dispersion of fillers therein through reflected light measurement (RLM) methods. The present disclosure also provides a device for practicing this improved method. Use of the device and/or practice of this method facilitate dispersion testing of unvulcanized rubber, such that the device and method are suitable for process and quality control testing purposes. Although not necessary, the device and method of the present invention are preferably employed to rate the filler dispersion within a sample of compounded rubber taken from the masterbatch in rubber manufacturing process. The dispersion ratings for the fillers within cut samples of compounded rubber prepared from a master batch according to the present invention correlate with the energy consumed during the mixing of the masterbatch; the processability, as indicated by the Mooney viscosity and Mooney stress relaxation of the final compound, and; the dispersion rating of the final vulcanizate. Also, the method herein advantageously provides a dispersion rating for, preferably, a masterbatch sample of compounded rubber within a very short amount of time (approx. 1–5 minutes), such that the method herein can be used concurrently with common production processes, and out of specification dispersion ratings within the masterbatch allow the batch to be held and/or adjusted before additional processing.

As mentioned, the present device and method focus on the RLM method for analyzing the dispersion of fillers throughout a sample of compounded rubber. Particularly, the present invention focuses on improving the process for preparing cut samples for RLM, by minimizing or eliminating the presence of depressions within a cut surface that are the result of entrapped air within a rubber sample, and also by minimizing or eliminating the presence of depressions or bumps on a cut surface resulting from smearing of the cut surface during the cutting operation.

As already defined herein, compounded rubber is to be understood as a natural or synthetic rubber that is mixed, as conventionally know, with at least a reinforcing filler, such as carbon black, and optionally, with other additives commonly mixed with such rubbers, such as processing aids, vulcanizing aids, pigments, plasticizers, etc. Inasmuch as the device and method of the present invention serve to facilitate the measurement of the dispersion of fillers within a rubber, compounded rubbers, for the purposes herein, must contain a reinforcing filler. Aside from this criteria, virtually any type of compounded rubber may be manipulated an analyzed with the device and method of this invention.

Non-limiting examples of these rubbers include natural rubbers and synthetic rubbers, such as styrene-butadiene (SBR), and ethylene propylene diene terpolymers (EPDM), among others.

Non-limiting examples of the types of reinforcing fillers that may be compounded with rubbers and thereafter analyzed according to the present invention include carbon black and silicas, among others.

Compounded rubbers, as defined herein, may include reinforcing fillers in various amounts. However, the weight ratio of fillers within the compounded rubber is not germain to the present invention. Rather, the purpose of the present invention is to provide a device and method for measuring filler dispersion, within a compounded rubber sample, against a desired standard according to the RLM method.

Although the device and method herein may be used to measure the dispersion of fillers within a cured compounded rubber sample (i.e., vulcanizate), they are preferably employed with a compounded rubber sample coming off of the masterbatch in the rubber manufacturing process. Advantageously, the present invention can be practiced in a span of time that is commensurate with production processes for rubber products (approx. 4–6 minutes). Generally, the method involves two steps: pressing a sample of rubber compounded with fillers and, preferably, cooling the sample during the pressing operation; and cutting the sample at the pressed portion thereof while the sample is being subjected to a dynamic pulling force. The present invention also provides a device for carrying out this method.

To begin the process, a sample of compounded rubber is obtained from the mixing apparatus used to mix a base rubber with the compounding ingredients. Such mixing apparatus may include Braebender mixers and rubber mills, among other devices.

After sheeting or extruding from the mixing apparatus, a sample of compounded rubber is cut for the purpose of preparing a cut sample for reflected light measurement of the dispersion of fillers therein. The sample is then taken for pressing (preferably, pressing and cooling) and cutting to prepare a cut surface.

As a consequence of the mixing operation, the compounded rubber contains many microscopic entrapped air bubbles. If not removed from the sample of compounded rubber, these entrapped air bubbles will present depressions on the cut surface of the sample that will falsely indicate the presence of reinforcing fillers when analyzed by RLM methods. Thus, the sample of compounded rubber taken off the mixing apparatus is first pressed at a portion thereof that is to be cut so as to remove entrapped air. The rubber sample coming off of the mixing apparatus is hot (approx. 70° C. to 150° C.), and this facilitates the pressing operation; however, it is preferred that the sample, once pressed and cut according to the method herein, be sufficiently cooled before the sample is subjected to reflected light measurement. Preferably, the sample is to be cooled to a temperature preferably less than about 35° C. Thus, the method of the present invention preferably provides for the cooling of the sample.

The sample of compounded rubber can be pressed in virtually any manner so as to remove the presence of entrapped air at a portion thereof. Generally, the sample is pressed by mechanical force so as to be compressed by at least 25%, although this invention is not to be limited thereto or thereby. This pressing step is somewhat generic to the art, but the method of the present invention improves thereon by teaching to preferably cool the sample during pressing in order to speed up the sample analysis to help ensure that it may be run concurrently with the production process.

Figure 3:
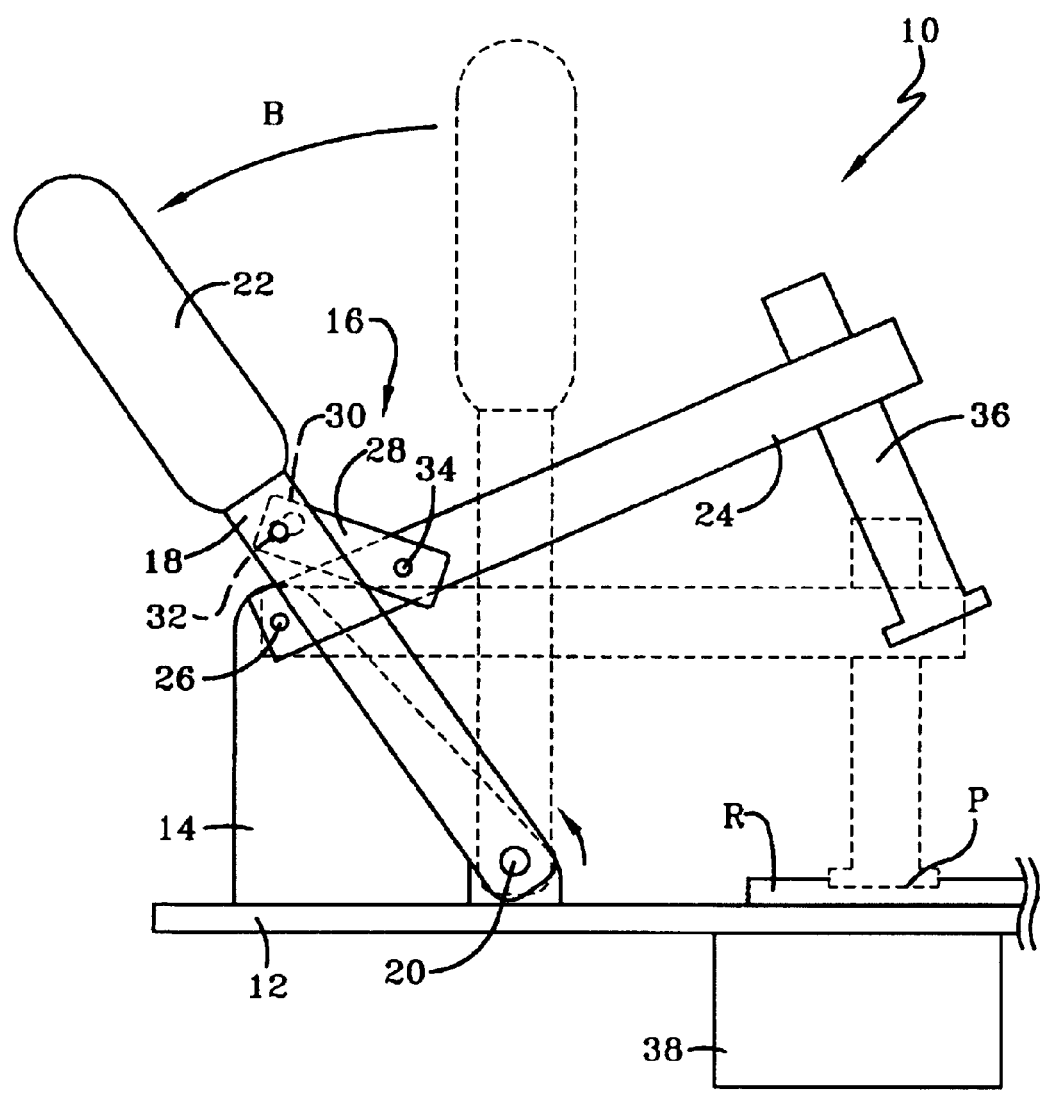
FIG. 3 is a side plan view of a sample press according to this invention.

Referring now to FIG. 3, a sample press is designated therein by the numeral 10. Sample press 10 includes base plate 12 having affixed thereto a fulcrum support 14, which supports a locking clamp that is generally represented by the numeral 16. Clamp 16 includes lock arm 18, which is pivotally connected near the base of fulcrum support 14 at an appropriate bearing 20. Handle 22 is provided for manipulating lock arm 18. Lever arm 24 pivotally attaches near the top of fulcrum support 14 at an appropriate bearing 26, and is operatively connected to lock arm 18 by lock plate 28. Lock plate 28 includes a dogbone channel 30 that communicates with lock arm 18 through a pin 32, and connects to lever arm 24 through bearing 34. Press 36 extends downwardly and perpendicularly from lever arm 24.

In FIG. 3, sample press 10 is shown in the un-clamped position and in the clamped position, the clamped position being shown in phantom. In the clamped position as shown in phantom in FIG. 3, press 36 is brought into close proximity to base plate 12 so as to press a portion P of a sample of compounded rubber designated by the letter R. In this position, pin 32, exerts a locking force on lever arm 24 and press 36 by bearing down upon the lower surface of dogbone channel 30, in lock plate 28, so as to put pressure on bearing 34, which communicates with lever arm 24.

In the unclamped position of FIG. 3, handle 22 is pulled in the direction of arrow B, causing pin 32 to move within dogbone channel 30 to bear upon the upper surface thereof, releasing some of the locking force, and raise lever arm 24 and press 36, as shown. It should be mentioned that it is not necessary that the press employed in this step be a locking press; however, the locking press taught herein is useful because it may also be employed in cutting the sample of compounded rubber at the pressed portion thereof.

Advantageously, the present invention teaches that the sample of compounded rubber be cooled during the pressing step. As mentioned, it is preferred that the sample be cooled from its relatively hot temperature off of the mixing apparatus before being analyzed by reflective light measurement. Cooling is achieved in the device of the present invention by providing a cooling element, generally represented by the numeral 38 beneath space plate 12. Cooling element 38 serves to cool base plate 12 and, during pressing of the sample of compounded rubber, R, cools the sample to a more appropriate temperature for reflected light measurement of the filler dispersion.

Once the sample has been pressed at a portion thereof to remove entrapped air, the pressed portion is cut while being subjected to a dynamic pulling force. By "a dynamic pulling force" it is meant that the elements pulling the sample are dynamically moving, as opposed to having strained the sample and then gone static before the cutting operation. Thus, the sample is cut concurrently as it is strained by pulling the ends of the sample away from each other. By cutting during application of a dynamic pulling force, the cut surface of the sample that is produced during the cutting operation will exhibit minimal, if any, smearing. It has been found that there is a greater tendency for smearing on a cut surface when the sample is either cut under no special conditions (i.e., no pulling force) or is cut subsequently to allowing a pulling force to go static.

Generally, the sample is subjected to a dynamic pulling force simply by grasping opposed ends of the sample and pulling those ends apart at a constant rate. Obviously, this pulling can occur through a number of methods. For instance, one end of the sample could be clamped by a stationary device, while the other end is clamped to a device that moves relative to the stationary device, or each end of the sample could be clamped to mobile device such that neither end is stationary but is rather pulled away from its opposed end. To ensure a good, consistent cut, the pulling preferably occurs at a constant rate. Additionally, it is preferred that each end of the sample be pulled, i.e., no end is clamped to a stationary device, thereby providing a straighter cut. It is also preferred that the cutting of the sample not begin until the sample has been strained by about 5 to 10% by the dynamic pulling force. The pulling rate and the rate at which a cutting instrument is advanced through the sample should be adjusted for different types of compounded rubbers in order to ensure that the sample is not ripped, but is rather smoothly cut by cutting under a dynamic pulling force.

It has also been found that there is less of a tendency for smearing if the sample is cut in air, and not against a back plate. The action of a cutting blade that presses against a sample that is up against a back plate tends to compress and bunch the rubber up against the back plate, resulting in a cut surface that is not smooth. Thus, the ends of the sample are preferably pulled apart with a dynamic pulling force, while a cutting blade cuts the pressed portion thereof in air.

Figure 4:
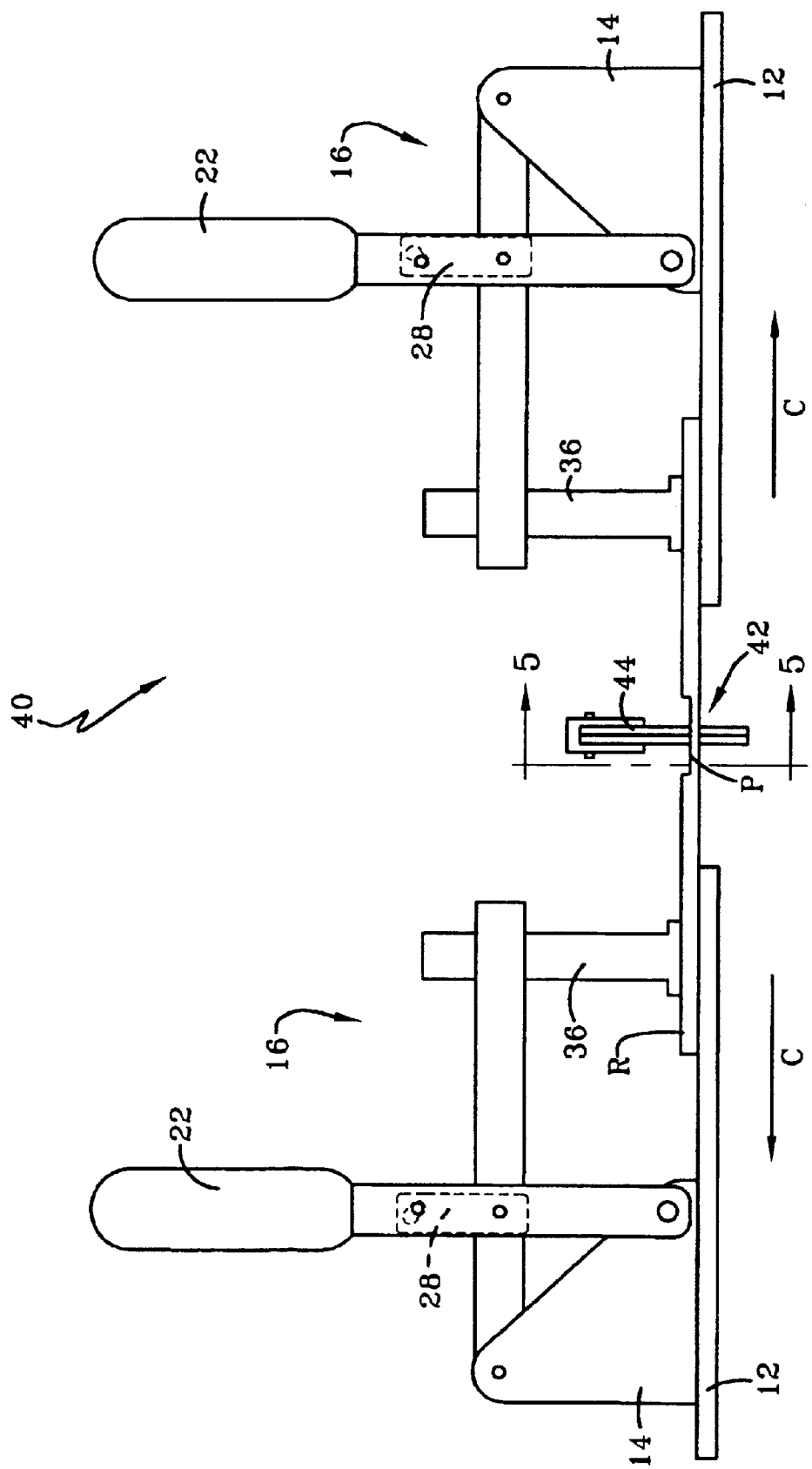
FIG. 4 is a front plan view of a cutting device according to the present invention for the improved preparation of a cut surface in a compounded rubber sample.

A device for carrying out this method, and employing sample presses 10 as clamps, is generally depicted in FIG. 4. Therein, portions of the sample press have received like numerals as described above. The cutting device of FIG. 4 is generally represented by the numeral 40. The cutting device 40 includes opposed clamps 16 operatively connected to fulcrum supports 14. The opposed clamps 16 serve to clamp a sample of compounded rubber R across a gap 42 so as to position pressed portion P of sample R to be cut "in air" as described above. Cutting blade 44 serves to cut sample R at pressed portion P.

In accordance with the method taught herein, cutting device 40 is operated to cut sample R while sample R is being subjected to a dynamic pulling force. Particularly, the clamps 16 and their associated base plates 12 are activated to move at a constant rate and thereby exert a pulling force on sample R, as represented by arrows C. As the clamps 16 move in the direction of arrows C and exert the dynamic pulling force on sample R, cutting blade 44 advances through pressed portion P. The movement of cutting blade 44 will be better appreciated with reference to FIG. 5. It should be appreciated that although preferred, both clamps 16 need not move to exert the dynamic pulling force, i.e., one clamp 16 could remain stationary while the other clamp 16 moves relative thereto. Movement of both clamps 16 is preferred, since such movement has been found to help create more satisfactory cuts in a sample.

Figure 5:
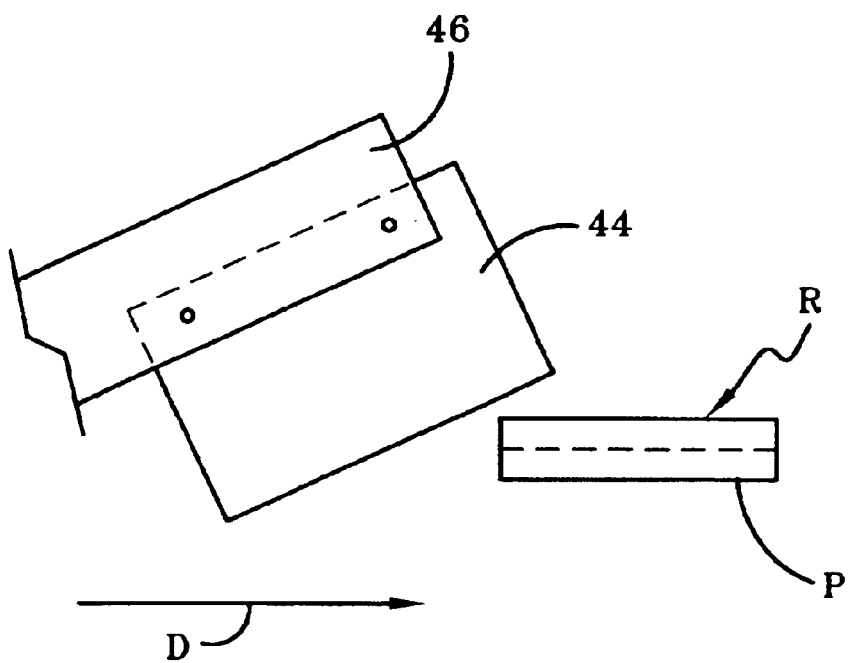
FIG. 5 is a side plan view taken generally along the line 5—5 in FIG. 4, showing the cutting blade more particularly.

FIG. 5 shows that cutting blade 44 is connected to a driving force (not shown) by an extension 46. Activation of the movement of cutting blade 44 occurs substantially concurrently with activation of the relative movement of clamps 16, so that cutting blade 44 is advanced in the direction of arrow D and cuts through the pressed portion P of sample R while sample R is being subjected to a dynamic pulling force. The angled orientation of cutting blade 44 in relation to sample R facilitates the cutting operation.

Thus, the method herein serves to prepare cut surfaces in a sample of compounded rubber for the purposes of analyzing the dispersion of fillers therein through reflected light measurement. The method minimizes the presence of irregularities on the cut surface that are the result of either entrapped air or smearing. As a result, the subsequent reflected light measurement of the dispersion of fillers will be more accurate. Additionally, the method herein is employed on rubber samples coming off of the coming off the master batch, i.e., on rubber samples that do not include accelerators and curing agents. It has been found that the dispersion rating of the masterbatch correlates with the energy consumed during the mixing of the masterbatch, the processability, as indicated by Mooney viscosity and Mooney stress relaxation of the final compound, the dispersion and rating of the final vulcanizate. Advantageously the dispersion rating of the masterbatch sample can be obtained in about 4–5 minutes, such that the dispersion rating of the masterbatch is ideally suited to supply intermediate data that can be used to monitor the mixing process. This can lead to savings in energy consumption, mixer overhead, and, ultimately, improved final product quality.

EXPERIMENTAL

Description of Apparatus and Instrumentation

The disperGRADER Model 1000NT (Tech Pro) was used for the dispersion measurement. This model has several scales available for comparison. The scale that was selected for these tests was the RCB scale. This scale is typically used for measurement of compounds filled with reinforcing carbon black. Ten reference pictures are used for determining the dispersion rating (DR). These reference pictures represent continuous improvements in dispersion from the poorest being 1 to the best being 10. An algorithm has been derived using these reference pictures and is then applied to an unknown sample. The disperGRADER then analyzes an unknown sample and automatically assigns a DR to the unknown sample. The analysis allows dispersion ratings to be less than 1 and greater than 10. Higher DR represent better dispersion. Visual comparison is seen on a computer monitor. The unknown specimen is shown on one half of the screen and the reference picture is displayed simultaneously adjacent to it. The numerical value of DR is shown on the screen and output to a separate computer for further analysis.

Samples were pressed and cut according to the device and marked herein.

Mooney viscosity and Mooney relaxation tests were run according to ASTM D 1646 using the TECH PRO viscTECH+(Tech Pro.

Overview

A natural rubber formulation shown in Table I was chosen for evaluation. The experiment was designed to mix a masterbatch at various conditions of rubber breakdown and filler incorporation times as shown in Table II. Dispersion was measured on the masterbatch and the results compared to various properties of the final compound and vulcanizate.

TABLE 1

Formulation for Compound TPI

| INGREDIENT | PHR |
|---|---|
| SMR 5 | 100.0 |
| N330 Black | 45.0 |
| 6 PPD | 1.5 |
| TMQ | 1.5 |
| Stearic Acid | 2.0 |
| Zinc Oxide | 3.0 |
| Sulfur | 1.5 |
| MBS | 1.5 |
| TMTM | 0.2 |

TABLE II

Mixing Variations

| Batch Number | Rubber Breakdown Min. | Filler Mix Time Min. | Total Mix Time Min. |
|---|---|---|---|
| 1 | 1 | 5 | 6 |
| 2 | 1 | 6 | 7 |
| 3 | 1 | 7 | 8 |
| 4 | 1 | 8 | 9 |
| 5 | 1 | 9 | 10 |
| 6 | 1 | 11 | 12 |
| 7 | 1 | 13 | 14 |
| 8 | 0 | 6 | 6 |
| 9 | 0 | 11 | 11 |
| 10 | 2 | 7 | 9 |
| 11 | 2 | 9 | 11 |
| 12 | 3 | 5 | 8 |
| 13 | 3 | 8 | 11 |
| 14 | 3 | 13 | 16 |
| 15 | 5 | 7 | 12 |
| 16 | 5 | 9 | 14 |
| 17 | 7 | 6 | 13 |
| 18 | 7 | 8 | 15 |
| 19 | 7 | 11 | 18 |

Procedures

The test formula, TPI, was mixed in a Farrel laboratory mixer, Size B. The nominal capacity of the mixer was 1.5 liter. Rotor speed was set at 77 rpm for both the masterbatch and final passes. The mixer was equipped with temperature and power recording devices. The final mix was intentionally undersized in order to minimize increased dispersion of the final. The batch weights of the masterbatch and final are given in Table III.

TABLE III

Batch Weights

| Ingredients | PHR | Batch Weight |
|---|---|---|
| Masterbatch | | |
| SMR5 | 100.0 | 840.0 |
| N330 Black | 45.0 | 378.0 |
| 6 PPD | 1.5 | 12.6 |
| TMQ | 1.5 | 12.6 |
| Stearic Acid | 2.0 | 16.8 |
| Zinc Oxide | 3.0 | 25.2 |
| Masterbatch Total | 153.0 | 1285.2 |
| Final | | |
| Masterbatch | 153.0 | 900.00 |
| Sulfur | 1.5 | 8.82 |
| MBS | 1.5 | 8.82 |
| TMTM | 0.2 | 1.18 |
| Final Total | 156.2 | 918.82 |

Nineteen batches of the formula TPI were mixed according to the mix cycle variations given in Table II. The basic mix procedures for the masterbatch and final are shown in Table IV. After each pass the compound was taken directly from the internal mixer to a 30.5×15.25 cm 2-roll mill. The mill nip was set at approximately 0.7 cm. The compound was passed through the mill, four (4) times without banding for sheeting purposes.

TABLE IV

Mixing Procedure

| Mixing Event | Occurs at: |
|---|---|
| Masterbatch | |
| Rubber breakdown | Time variable according to Table II |
| Filler and misc. ingredient mix time | Time variable according to Table II |
| Sweep at: | 2, 5, 3.75, 5.5 and 8 minutes where applicable |
| Drop batch at: | Total time according to Table II |
| Final: | |
| Breakdown MB | 1 minute |
| Add cure system | |
| Drop batch at: | 2.5 minutes |

The procedure for the second/final pass varied slightly. Since the batch was undersized, 200 grams of the masterbatch were milled to approximately 0.3 cm. The cure system was then placed in the middle of this milled sheet and the sheet folded to create an accelerator "pocket". This helped ensure that the entire cure package was mixed into the final compound.

Immediately after sheeting from the mill a strip of the compound, approximately 12×2 cm, was cut and placed in the sample press. The sample was still hot at this time. When the samples were cool they were cut using the uncured sample cutter and tested for dispersion.

Compression set buttons were cured for use in the dispersion rating measurements of the cured specimens. The cure was 15 minutes at 154° C. These samples were cut using the standard sample cutter supplied with the disperGRADER.

Mooney viscosity and stress relaxation tests were run at 100° C. using the large rotor. Viscosity measurements were taken at 4 minutes, and stress relaxation measurements were run for an additional 3 minutes. ML1+4 was taken for the viscosity measurement and t80 for the Mooney stress relaxation measurement. The t80 result is the time that it takes the viscosity to drop 80% after the rotor stops.

The dispersion ratings were made using the disperGRADER 1000NT, 100×magnification. The scale used for comparison was the RCB scale. Three measurements were taken on each cut and the average reported for the result. The sample was cooled in about 3–4 minutes. The cutting and measurement operation took approximately 1 minute.

Results and Discussion

The dispersion rating results, mixing data, Mooney viscosity arid Mooney relaxation data are given in Table V.

TABLE V

Experimental Results

| Batch No. | Filler Mix Time (min) | Rubber Mix Time (min) | Total Mix Time (min) | Dispersion MB DR | Dispersion Cured DR | Work Input MB, MJ | Final Mooney Data ML1 + 4 | Final Mooney Data t80 (min) |
|---|---|---|---|---|---|---|---|---|
| 1  | 5  | 1 | 6  | −3.94 | 6.99  | 4.384  | 103.0 | 0.79 |
| 2  | 6  | 1 | 7  | −1.62 | 7.77  | 5.368  | 101.1 | 0.64 |
| 3  | 7  | 1 | 8  | 2.20  | 9.09  | 5.976  | 99.9  | 0.54 |
| 4  | 8  | 1 | 9  | 2.61  | 9.18  | 6.588  | 93.6  | 0.42 |
| 5  | 9  | 1 | 10 | 3.89  | 9.31  | 7.455  | 89.3  | 0.32 |
| 6  | 11 | 1 | 12 | 6.26  | 9.48  | 9.338  | 80.3  | 0.24 |
| 7  | 13 | 1 | 14 | 7.92  | 9.62  | 1.797  | 73.3  | 0.21 |
| 8  | 6  | 0 | 6  | −3.02 | 7.55  | 3.883  | 104.6 | 1.05 |
| 9  | 11 | 0 | 11 | 3.90  | 9.27  | 8.775  | 75.9  | 0.22 |
| 10 | 7  | 2 | 9  | 4.50  | 9.34  | 6.973  | 92.9  | 0.38 |
| 11 | 9  | 2 | 11 | 5.42  | 9.47  | 8.168  | 91.0  | 0.36 |
| 12 | 5  | 3 | 8  | 1.67  | 8.23  | 5.891  | 99.9  | 0.53 |
| 13 | 8  | 3 | 11 | 6.98  | 9.50  | 8.168  | 90.9  | 0.34 |
| 14 | 13 | 3 | 16 | 7.91  | 9.88  | 11.180 | 79.2  | 0.23 |
| 15 | 7  | 5 | 12 | 5.38  | 9.00  | 8.509  | 88.4  | 0.33 |
| 16 | 9  | 5 | 14 | 7.18  | 9.90  | 9.912  | 79.6  | 0.26 |
| 17 | 6  | 7 | 13 | 6.58  | 9.49  | 8.511  | 86.7  | 0.32 |
| 18 | 8  | 7 | 15 | 7.05  | 9.74  | 10.078 | 81.5  | 0.26 |
| 19 | 11 | 7 | 18 | 9.15  | 10.12 | 12.442 | 74.9  | 0.22 |

(1) Comparison of Masterbatch Dispersion Rating to Work Input of the MB

Since work input can be considered a primary measure of mixing, the relationship of the dispersion rating of the masterbatch can be compared to the work input of the masterbatchs. For example, a typical factory mix would keep the rubber breakdown constant and the majority of mixing variation would occur after filler and other ingredients are added. Compounds 1 to 7 in this study keep the rubber breakdown the same at 1 minute but dramatically vary the filler mix time. The comparison of the dispersion rating of the masterbatch and mixing energy is shown in FIG. 6. As would be expected these results indicate a good correlation between dispersion rating and work input of the masterbatch. It is expected that the DR would reached a maximum level at some work input level, and a log linear regression analysis was therefore used rather than a linear analysis.

Batches 8 through 17 vary not only the filler mix time, but also the natural rubber breakdown time. The dispersion rating of all masterbatches were compared to the work input in FIG. 7. Even here, where both the rubber breakdown and mixing time of the filler are varied, there is a good correlation between dispersion rating and work input in the masterbatch. The correlation reinforces the concept that dispersion is not only related to the mixing time of the fillers, but also other factors, including the wetting of the filler by the polymer.

(2) Comparison of Dispersion Rating to Processing Characteristics

Seeing that the dispersion rating correlates to the work input of the mix, the next step analyzed how the dispersion rating relates to the processability of the final compound. As above, batches 1 to 7 were used for comparison since only the filler mix time was varied. For this comparison Mooney viscosity tests and Mooney stress relaxation tests were run. It has been shown that the Mooney stress relaxation values are a good indicator of processability even when Mooney viscosity values are similar. FIG. 8 shows the correlation of the dispersion rating to Mooney viscosity. FIG. 9 shows the relationship of the dispersion rating to Mooney stress relaxation. Both Mooney viscosity and Mooney stress relaxation relate well to the dispersion.

The correlation of the dispersion rating to Mooney data is important in two respects:

1. The DR correlated well with not only the Mooney viscosity, but also the work input. This suggests that this method of dispersion rating may be used as a quantification of the mix cycle.
2. The improved correlation of the dispersion rating to Mooney stress relaxation suggests that, since t80 is a measure of the compound's elasticity, DR is a better indicator of processability than just the Mooney viscosity.
3. Comparison of the Dispersion Rating of the Masterbatch vs. Final Vulcanizate.

The dispersion rating of the masterbatch and the vulcanizate are shown in FIG. 10, which shows good correlation.

The literature has explicitly shown that dispersion directly relates to the physical properties of the cured products. The results obtained from dispersion rating analysis of these 19 batches indicate that the dispersion rating of the masterbatch does correlate with that of the vulcanizate. In this case then, a process control parameter of dispersion rating could be assigned to the masterbatch which would indicated the properties of the vulcanizate.

Example of Dispersion Rating Used for Process Control

The effect of the dispersion on physical properties of the vulcanizate varies depending on the polymer, filler and other compounding ingredients. In general, it has been seen that longer mixing and, therefore, better dispersion, lowers the Payne effect, lowers E', E", hardness and in some cases lowers modulus. Longer mixing, in general, increases tensile strength, tear resistance, fatigue resistance, improves cut growth resistance but increases bound rubber. Other vulcanizate properties such as hysterisis, heat build up, and permanent set are properties that relate to tan. These are of great interest to both the properties of processability, i.e. die swell, and the finished product. Studies have shown these tan 8 related properties to improve with mixing in some compounds, to degrade in other compounds 20, and in some to actually reverse their effect during the mix. These general relationships are shown in FIG. 11. It is clear, that to achieve the required vulcanizate properties, the mix cycle must be optimized. Once the optimum mix is established, a dispersion rating can be assigned and limits attached. As related to the process, the lower limit is the minimum DR allowed to achieve the required properties. The upper limit brackets the required properties and limits the mixing time to maximize profits.

The results of this study indicate that the dispersion rating of the masterbatch can be used to predict the dispersion rating of the vulcanizate even before the final compound is mixed. That is, the dispersion rating of the masterbatch indicates the dispersion rating of the final vulcanizate and therefore it's physical properties. Other factors not related to filler dispersion may also further influence the vulcanizates' properties and this would be the reason to continue to fingerprint the final mix with a test such as the curemeter. With dispersion testing of the masterbatch in place then, the curemeter fingerprint would indicate what it does best, the curing characteristics.

To go back one step further in the process, consider using the dispersion rating directly after mixing the masterbatch for statistical process control (SPC). An example of this type of Individuals Chart is shown in FIG. 12. Here +/−3 sigma may be assigned according to standard SPC practices along with the specification limits described. Trends and out of control situations may be detected and used to correct and adjust the mixing process. The advantages of control applied to the masterbatch are two-fold:

1. If the DR is out of specification on the low side, then the batch needs to be held or mixed further to achieve the proper final dispersion level.
2. If the DR is out of control on either the low or high side, or out of specification on the high side, then the mixing process needs to be reviewed.

SPC control of the masterbatch dispersion rating provides a tool for evaluating the mixing cycle in order to achieve maximum economy of the mixing process and consistent vulcanizate quality.

Process and quality control tests are essential parts of manufacturing. Process controls help assure proper procedures and improve product quality. In typical two pass mixes, testing of the masterbatch must be easy, fast, and must relate to the mixing process, the forming process and the final product. The described method of rating the dispersion of the masterbatch was shown to:

1. Correlate with the energy consumed during the mix of the masterbatch.
2. Correlate to the processability as indicated by the Mooney viscosity and Mooney stress relaxation of the final compound.
3. Correlate to the dispersion rating of the final vulcanizate.
4. Provide a dispersion rating in 4–5 minutes including time to cool, cut and test the sample.

Use of the dispersion rating of the masterbatch is ideally suited to supply an intermediate set of data that can be used to monitor the mixing process, allowing savings in direct energy consumption, mixer overhead, and, ultimately, improved final product quality.

Thus it can be seen that the objects of the invention have been satisfied by the structure presented herein above. While in accordance with the patent statutes only the best mode and preferred embodiment of the invention has been presented and described in detail, the invention is not limited thereto or thereby. Accordingly, for an appreciation of the scope and breadth of the invention reference should be made to the following claims.

What is claimed is:

1. A method for conducting a reflected light measurement of the dispersion of fillers in a sample of compounded rubber comprising the steps of:

subjecting a sample of compounded rubber to a dynamic pulling force, the compounded rubber having reinforcing fillers therein;

cutting the sample while the sample is subjected to the dynamic pulling force, thereby creating a cut surface having bumps and indentations present as a result of the movement of the reinforcing fillers in said step of cutting the sample; and reflecting light off of the cut surface of the sample of compounded rubber whereby at least some of the light reflects off of the bumps and indentations to contact a sensor.

2. The method according to claim 1, wherein the sample of compounded rubber is cut in air in said step of cutting.

3. The method according to claim 1, further including the step of pressing a portion of the sample of compounded rubber, prior to subjecting the sample to a dynamic pulling force, to free the pressed portion from entrapped air, the subsequent cutting occurring at the pressed portion of the sample.

4. The method according to claim 3, wherein the sample of compounded rubber is cooled concurrently with said step of pressing.

5. The method according to claim 1, wherein the sample of compounded rubber contains neither curing agents nor accelerators.

6. The method according to claim 1, wherein the dynamic pulling force is affected by pulling opposed ends of the sample of compounded rubber away from each other at a constant rate.

7. The method according to claim 1, wherein the sample of compounded rubber is strained by about five to ten percent by the dynamic pulling force before the cutting step begins.

8. The method according to claim 1, further comprising the step of preparing the sample of compounded rubber for said steps of subjecting to a dynamic pulling force and cutting by pressing a hot sample of the compounded rubber against a base plate having a cooling element that cools the base plate so as to speed the cooling of the hot sample of compounded rubber during the pressing thereof.

* * * * *